United States Patent
Meng et al.

(10) Patent No.: US 12,311,366 B2
(45) Date of Patent: May 27, 2025

(54) SAMPLE LOADING BOTTOM PLATE AND IMMUNOCHROMATOGRAPHY DETECTION APPARATUS CONTAINING SAMPLE LOADING BOTTOM PLATE

(71) Applicant: GUANGZHOU WONDFO BIOTECH CO., LTD., Guangzhou (CN)

(72) Inventors: Xuan Meng, Guangzhou (CN); Jiaming Du, Guangzhou (CN); Xirong Huang, Guangzhou (CN)

(73) Assignee: GUANGZHOU WONDFO BIOTECH CO., LTD., Guangzhou (CN)

( * ) Notice: Subject to any disclaimer, the term of this patent is extended or adjusted under 35 U.S.C. 154(b) by 970 days.

(21) Appl. No.: 17/421,854

(22) PCT Filed: Jul. 31, 2019

(86) PCT No.: PCT/CN2019/098729
§ 371 (c)(1),
(2) Date: Jul. 9, 2021

(87) PCT Pub. No.: WO2020/143219
PCT Pub. Date: Jul. 16, 2020

(65) Prior Publication Data
US 2022/0105508 A1    Apr. 7, 2022

(30) Foreign Application Priority Data
Jan. 11, 2019    (CN) .................... 201910027921.X (51) Int. Cl.
*B01L 3/00*    (2006.01)
*B01L 9/00*    (2006.01)
(Continued)

(52) U.S. Cl.
CPC ......... *B01L 3/50273* (2013.01); *B01L 3/5023* (2013.01); *B01L 9/527* (2013.01);
(Continued)

(58) Field of Classification Search
CPC .... B01L 3/50273; B01L 3/5023; B01L 9/527; B01L 2200/021; B01L 2200/028;
(Continued)

(56) References Cited

U.S. PATENT DOCUMENTS 6,153,148 A    11/2000  Thomas
6,875,185 B2    4/2005  Wong et al.
(Continued)

FOREIGN PATENT DOCUMENTS

CN    201025480 Y    2/2008
CN    203287379 U    11/2013
(Continued)

OTHER PUBLICATIONS

International Search Report, and English Translation thereof, and Written Opinion for International Application No. PCT/CN2019/098729, mailed Nov. 1, 2019 (13 pages).
(Continued)

*Primary Examiner* — Samuel P Siefke
*Assistant Examiner* — Alea N. Martin
(74) *Attorney, Agent, or Firm* — Kagan Binder, PLLC (57) ABSTRACT

A sample loading bottom plate (300, 600, 810, 820, 831) and an immunochromatography detection apparatus (10) containing the sample loading bottom plate (300, 600, 810, 820, 831). During design of the sample loading bottom plate (300, 600, 810, 820, 831), a sample loading portion (310, 833) having a multistage-step structure is additionally provided on a sample loading region and comprises multistage steps having different heights, wherein a base surface (311) is used for carrying a sample solution. After a cover plate (100, 500, 834) is covered, the sample solution falls on the base surface (311) and then flows upwardly, and by means of the flow-intercepting and buffering effects of the multistage-step structure, the sample solution which finally flows
(Continued)

to a top surface (342, 642) of the highest step (340, 640) can basically flow to sample loading regions of immunochromatography detection members synchronously, so that the multiple immunochromatography detection members can basically receive the sample solution synchronously, the unifying problem of time and sample horizontal lines is solved, and the test accuracy is high; moreover, only one-time sample adding is needed, the detection efficiency is high, and the risk of errors is low. During detection, the immunochromatography detection members perform detection individually and perform sample loading synchronously without mutual interference, and the accuracy of a detection result is high.

17 Claims, 7 Drawing Sheets (51) Int. Cl.
  *G01N 33/543* (2006.01)
  *G01N 33/558* (2006.01)
(52) U.S. Cl.
  CPC . *G01N 33/54388* (2021.08); *G01N 33/54391* (2021.08); *G01N 33/558* (2013.01); *B01L 2200/021* (2013.01); *B01L 2200/028* (2013.01); *B01L 2200/16* (2013.01); *B01L 2300/042* (2013.01); *B01L 2300/0825* (2013.01); *B01L 2300/0887* (2013.01); *B01L 2400/0406* (2013.01)
(58) Field of Classification Search
  CPC ........... B01L 2200/16; B01L 2300/042; B01L 2300/0825; B01L 2300/0887; B01L 2400/0406; G01N 33/54388; G01N 33/54391; G01N 33/558; G01N 33/54387; G01N 33/543
  See application file for complete search history.

(56) References Cited

U.S. PATENT DOCUMENTS

2008/0161769 A1 7/2008 Howell et al.
2008/0317633 A1 12/2008 Sibbett et al.
2013/0280698 A1 10/2013 Propper et al.
2015/0010916 A1 1/2015 Chuang et al.
2017/0160263 A1 6/2017 Hvichia
2022/0099668 A1 3/2022 Meng et al.

FOREIGN PATENT DOCUMENTS

| CN | 204203230 U | | 3/2015 |
|---|---|---|---|
| CN | 204666636 U | | 9/2015 |
| CN | 205426921 U | | 8/2016 |
| CN | 106053803 A | | 10/2016 |
| CN | 106442978 A | | 2/2017 |
| CN | 206038690 U | * | 3/2017 |
| CN | 108072757 A | | 5/2018 |
| CN | 108802402 A | | 11/2018 |
| CN | 109557304 A | | 4/2019 |
| CN | 109580938 A | | 4/2019 |
| DE | 202014002369 U1 | | 4/2014 |
| EP | 2120048 A1 | | 11/2009 |
| JP | 5526428 A | | 2/1980 |
| JP | S56125663 A | | 10/1981 |
| JP | 2006058280 A | | 3/2006 |
| JP | 2006087325 A | | 4/2006 |
| JP | 2017530336 A | | 10/2017 |
| WO | 2013163353 A1 | | 10/2013 |
| WO | 2015017591 A1 | | 2/2015 |
| WO | 2020143220 A1 | | 7/2020 |

OTHER PUBLICATIONS

Non-Final Office Action for U.S. Appl. No. 17/422,004, mailed Jun. 15, 2023, (39 pages).
Japanese Decision to Grant, and English translation thereof, for Japanese counterpart Application No. 2021-540187, mailed Nov. 8, 2022 (5 pages).
Extended European Search Report for European counterpart Application No. 19908785.9, mailed Mar. 14, 2022 (7 pages).
Japanese Office Action, and English translation thereof, for Japanese counterpart Application No. 2021-540187, mailed Jun. 21, 2022 (8 pages).

* cited by examiner

SAMPLE LOADING BOTTOM PLATE AND IMMUNOCHROMATOGRAPHY DETECTION APPARATUS CONTAINING SAMPLE LOADING BOTTOM PLATE

TECHNICAL FIELD

The present disclosure relates to the field of in vitro diagnostics, in particular to a sample loading baseplate and an immunochromatographic assay device comprising the same.

BACKGROUND

In the field of in vitro diagnostics (IVD), chromatography is often used for diagnosis and test for diseases and other matters. For example, principles of chromatography are used in an immunocolloidal gold test paper, a dry chemistry test paper, an immunofluorescence test paper, and the like to pre-process the sample, and then react with the reagents, and finally get a diagnostic result that reflects whether there is a disease. The fluorescence immunochromatographic test paper functions in a process as follows. After adding a sample (whole blood, plasma, and the like) onto a sample pad, the liquid flows toward an end of a water absorbent filter paper. In the sample pad, the sample is processed for filtering of red blood cells, removing of interferences, and the like. The sample then flows through a conjugate pad where antigens immunologically bind to antibodies, with fluorescent groups conjugated. The sample subsequently flows through a nitrocellulose membrane where the immunocomplex specifically binds to the antigen and antibody bound on the nitrocellulose membrane in advance, and the fluorescent groups gathered on the test line and the control line can show the test result. Other unbound interferences are absorbed by the water absorbent filter paper. Fluorescence immunochromatography has been widely used in the field of POCT assay in recent years, since it has the characteristics of simple operation, strong specificity, high sensitivity, quantifiability and the like. However, in recent decades, the vast majority of immunochromatographic test cards can only be a single card with a single strip for a single item of test. However, with the development of medical technology, it is necessary for the diagnosis of diseases to detect multiple targets at once, for example in a myocardial 3-in-one test or myocardial 5-in-one test, in order to make the determination more accurate. In some cases, it is necessary to detect the condition of multiple organs simultaneously to determine diseases, for example in a cardiopulmonary 5-in-one test.

At present, many companies in and outside China are engaged in the research of a single card with a single sample addition for multi-item tests. For example, Alere Inc. has used a microfluidic chip to perform an in-series myocardial 5-in-one test on the chip. Although with advantages, this technology has obvious shortcomings, mainly due to the high cost and difficult processing of microfluidic chips, and easy interference between tests in series, and it belongs to microfluidic technology rather than immunochromatography. H-guard Biotech has been researching to perform in-series 3 items of testing on a fluorescence immunochromatographic test paper, but this method makes it insufficient in antibody immobilization and avoiding mutual interference between items. Bioson uses capillary shunting in a multi-card to drain a sample to a test paper, but it has difficulties in the processing of the capillary and the functions of the capillary can be easily affected by the impurities in the sample, and it is necessary to remove the barrier test paper after sample addition during operation of the card, which is not convenient to operate. Due to the above reasons, the multi-test card products on the market cannot be widely promoted.

SUMMARY

Based on this, it is necessary to provide a sample loading baseplate and an immunochromatographic assay device comprising the same, with a simple structure and small interference between assay components.

Provided is a sample loading baseplate comprising a sample loading portion; wherein the sample loading portion has a multi-step structure with a height increasing stepwise, wherein a datum surface located in the bottom of the multi-step structure is configured to receive the sample solution, and a highest step of the multi-step structure has a plurality of mounting positions configured to mount assay components, the adjacent mounting positions being arranged at intervals.

In one of the embodiments, when the sample loading portion is provided with a flat cover plate that is capable of covering the sample loading portion, and a sample solution is loaded to a position of the datum surface near its front end, the sample solution is capable of arriving at each of the mounting positions at substantially the same time after being intercepted and buffered by the multi-step structure.

In one of the embodiments, the test component is an immunochromatographic test paper with a sample loading zone located on the mounting position.

In one of the embodiments, the plurality of mounting positions satisfy at least one of the following requirements:
ends of the plurality of mounting positions are arranged flush;
the plurality of mounting positions are arranged in parallel; and
the adjacent mounting positions can be arranged at intervals of 1 mm to 4 mm.

In one of the embodiments, the datum surface and top surfaces of steps of the multi-step structure are all planar structures, and the datum surface is arranged in parallel with the top surfaces of the steps.

In one of the embodiments, the datum surface is an isosceles triangular shape whose bottom side is connected to a side surface of a lowest step.

In one of the embodiments, the top surface of the lowest step has a length gradually increasing as it approaches a higher step connected thereto.

In one of the embodiments, both ends of the top surface of the lowest step are arc-shaped, and the arcs at the both ends are symmetrically arranged.

In one of the embodiments, lengths of the top surfaces of the steps in the middle are kept consistent with the length all over the top surface of the highest step.

In one of the embodiments, a side surface of the highest step is a symmetrical cambered surface, and the cambered side surface gradually protrudes from both ends to the middle toward the position where the datum surface is located.

In one of the embodiments, the sample loading portion is a three-step structure.

Provided is an immunochromatographic assay device comprising a cover plate, immunochromatographic assay components, and a sample loading baseplate according to any one of the above embodiments; wherein the cover plate mates with the sample loading baseplate to define a testing cavity; a sample loading portion is located in the testing cavity; the cover plate is provided with a sample adding hole corresponding to a datum surface of the sample loading portion; and the immunochromatographic assay components are a plurality of immunochromatographic assay components, and sample loading zones of the plurality of immunochromatographic assay components are mounted on the plurality of mounting positions respectively.

In one of the embodiments, the sample adding hole is closed to an end of the datum surface far from the lowest step.

In one of the embodiments, the sample adding hole is arranged obliquely in its axial direction with respect to the cover plate.

In one of the embodiments, the sample adding hole has an inner diameter gradually decreased from an inlet end to an outlet end.

In one of the embodiments, the cover plate and the sample loading portion are spaced such that when the sample solution arrives at the space between the top surface of the highest step and the cover plate, the sample solution is capable of flowing along the surface of the sample loading portion toward the position where the sample loading zone of the immunochromatographic assay component is located under the propulsion of capillary action.

In one of the embodiments, a distance between the top surface of the highest step of the sample loading portion and the cover plate is not greater than 2 mm.

In one of the embodiments, each of the mounting positions is a long strip-shaped groove-shaped structure extending along the top surface of the highest step, configured to embed and mount a long strip-shaped immunochromatographic assay component.

In one of the embodiments, the immunochromatographic assay component comprises a substrate, and a sample pad, a conjugate pad, a testing membrane, and an absorbent pad that are arranged on the substrate and connected in turn from one end to the other end of the substrate, the sample pad has a sample loading zone, and the testing membrane has a test line.

In one of the embodiments, the cover plate is provided with testing windows configured to observe the test line of each of the immunochromatographic assay components.

In one of the embodiments, each of the mounting positions is a cylindrical hole structure with an axial direction perpendicular to the top surface of the highest step and with openings at both ends, configured to embed and mount an immunochromatographic assay component having a laminated structure; wherein the opening at the upper end is configured to allow the sample solution to flow into a sample loading zone, and the opening at the lower end constitutes a testing window.

In one of the embodiments, the immunochromatographic assay component comprises a supporting layer, a reaction layer, and a diffusion layer stacked in sequence, the diffusion layer having the sample loading zone and the reaction layer containing a reaction reagent capable of reacting with target substance and a color developing agent.

In one of the embodiments, the reaction layer comprises a reagent layer and a color developing layer that are stacked, and the color developing layer is closer to the supporting layer.

The reagent layer contains a reaction reagent capable of reacting with the target substance, and the color-developing layer contains a color developing agent; or vice versa.

In one of the embodiments, the cover plate is provided with a vent hole in a zone corresponding to the immunochromatographic assay component, communicating with the testing cavity.

For a multi-item test or a parallel test for the same item, it is better to use different or the same single-item immunochromatographic test papers and other immunochromatographic assay components for sample loading test, since the current development of testing techniques such as single-item immunochromatographic test papers and the like are more mature and their technology and craftsmanship are also perfect. Therefore, the immunochromatographic assay device of the present disclosure is designed on the basis of a plurality of single-item immunochromatographic assay components which are currently widely used. However, through research, it has been found that the main influencing factor of multiple immunochromatographic assay components during the test is that multiple sample loading are likely to cause difficulties in unification on time lines and samples parallel lines, which may have an impact on the accuracy of the test results, and multiple sample loading would reduce the testing efficiency and increase the risk of errors.

Therefore, in the design of the sample loading baseplate and the immunochromatographic assay device comprising the sample loading baseplate, the sample loading portion with a multi-step structure is added to the sample loading zone. The sample loading portion has multiple steps with different heights. The datum surface is configured to receive the sample solution. After the sample solution falls on the datum surface, it will flow upwards. Due to the interception and buffering effect of the multi-step structure, the sample solution that finally flows to the top surface of the highest step can arrive at the sample loading zone of each of the immunochromatographic assay components substantially at the same time, so that multiple immunochromatographic assay components can substantially receive the sample solution at the same time. There is no problem regarding the unity on time and sample parallel lines, rendering a high test accuracy. Also, sample loading is required only once, resulting in a high testing efficiency and relatively small risk of error. During a test performed by the immunochromatographic assay device, each of the immunochromatographic assay components performs the test independently and the sample is loaded at the same time. There is no mutual interference between the assay components, which is further conducive to increase the accuracy of the test result.

Not only that, the immunochromatographic assay device of the present disclosure is provided with a wetting zone with a certain length on the upstream of the sample loading zone of the immunochromatographic assay component. When the sample solution arrives at the wetting zone, capillary action will be produced to push the sample solution to flow in the wetting zone. This can not only increase the flow rate of the sample solution in this zone, but also realize the substantially simultaneous sample loading on the assay components in different mounting positions, which is beneficial to improve the consistency and uniformity of sample loading.

For the conventional multi-card immunochromatographic assay devices, it is difficult for the immunochromatographic assay components in different mounting positions to be loaded at the same time due to the inconsistency of sample loading. Also, nonuniform loading amount leads to only 3-in-one or 4-in-one test can be performed, and 5-in-one or more-in-one test can not be performed. Using the sample loading baseplate with the above-mentioned structure and/or controlling the distance between the sample loading baseplate and the cover plate to produce capillary action in the wetting zone, 5-in-one or 6-in-one test can be realized in the immunochromatographic assay device of the present disclosure with good consistency of sample loading and effectively improved accuracy and reliability of testing results.

DESCRIPTION OF REFERENCE NUMERALS

10: immunochromatographic assay device; 20: sample adding tube; 100, 500, 834: cover plate; 102, 502: testing cavity; 110: sample adding hole; 120: testing window; 200, 700, 832: immunochromatographic assay component; 210: substrate; 220: sample pad; 230: conjugate pad; 240: testing membrane; 242: test line; 250: absorbent pad; 300, 600, 810, 820, 831: sample loading baseplate; 310, 833: sample loading portion; 311: datum surface; 320: lowest step; 321: side surface of lowest step; 322: top surface of lowest step; 330: secondary step; 340, 640: highest step; 341: side surface of highest step; 342, 642: top surface of highest step; 510: vent hole; 710: supporting layer; 720: reaction layer; 721: reagent layer; 722: presentation layer; 730: diffusion layer.

DETAILED DESCRIPTION OF THE EMBODIMENTS

In order to facilitate the understanding of the present disclosure, the present disclosure will be described more comprehensively below with reference to the relevant drawings. Preferred embodiments of the present disclosure are shown in the drawings. However, the present disclosure can be implemented in many different forms and is not limited to the embodiments described herein. On the contrary, these embodiments are provided the purpose of making the understanding of the disclosure of the present disclosure more thorough and comprehensive.

It should be noted that in the case where an element is referred to as being "fixed to" or "installed on" another element, the element can be directly on the other element or an intervening element may also be present therebetween. In the case where an element is considered to be "connected" to another element, the element can be directly connected to the other element or an intermediate element may be present therebetween.

Unless otherwise defined, all technical and scientific terms used herein have the same meaning as commonly understood by those skilled in the technical field of the present disclosure. The terms used in the description of the present disclosure herein are only for the purpose of describing specific embodiments, and are not intended to limit the present disclosure. The term "and/or" as used herein includes any and all combinations of one or more related listed items.

Figure 1:
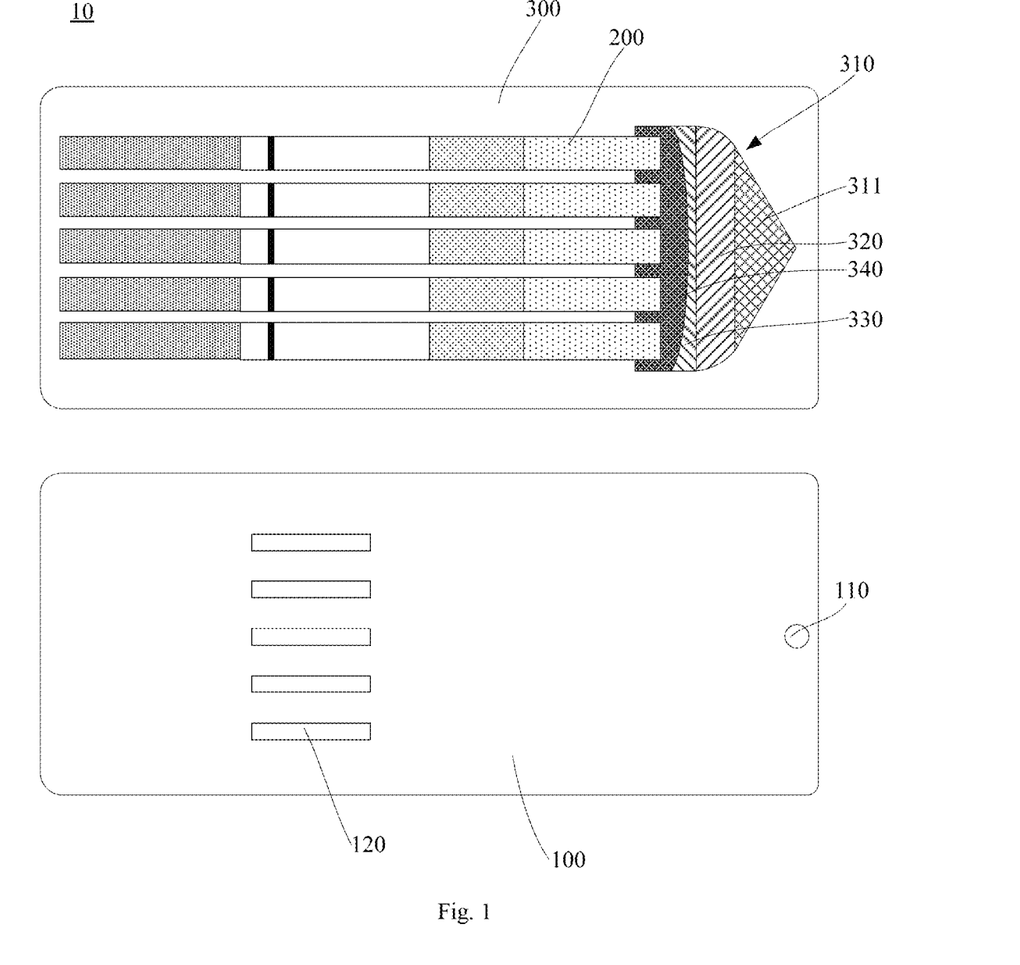
FIG. 1 is a partial exploded view of an immunochromatographic assay device according to an embodiment of the present disclosure.
Figure 2:
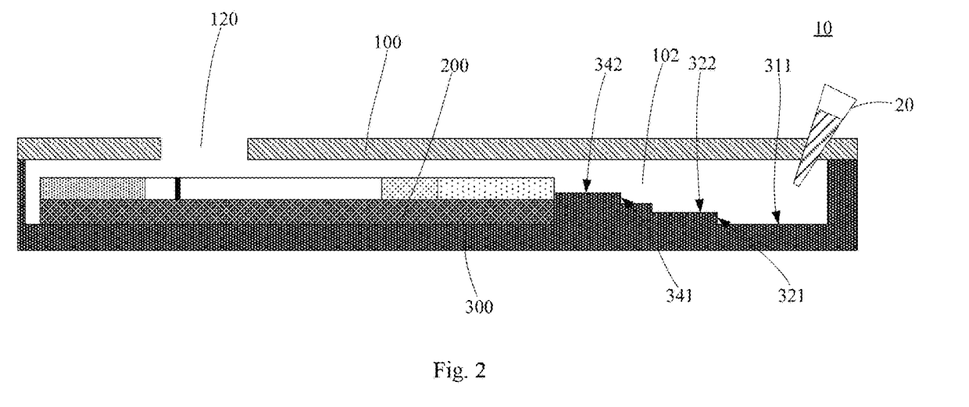
FIG. 2 is an after-assembly cross-sectional view of the immunochromatographic assay device shown in FIG. 1.
Figure 3:
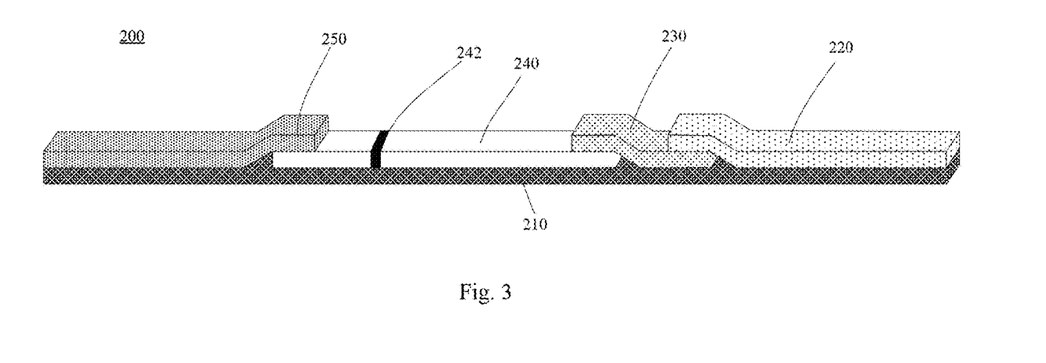
FIG. 3 is a structural schematic diagram of an immunochromatographic assay component in the immunochromatographic assay device shown in FIG. 1.

Referring to FIGS. 1, 2 and 3, an immunochromatographic assay device 10 is provided in an embodiment of the present disclosure, the immunochromatographic assay device 10 comprising a cover plate 100, immunochromatographic assay components 200, and a sample loading baseplate 300. The cover plate 100 mates with the sample loading baseplate 300 to define a testing cavity 102. The sample loading baseplate 300 has a sample loading portion 310. The sample loading portion 310 is located in the testing cavity 102. The cover plate 100 is provided with a sample adding hole 110 corresponding to the sample loading portion 310. The immunochromatographic assay components 200 are a plurality of immunochromatographic assay components 200 mounted on the sample loading baseplate 300 respectively.

Preferably, the sample adding hole 110 corresponds to an end of the sample loading portion 310 far away from the immunochromatographic assay components 200, so that a sample solution (such as blood, serum, saliva, etc.) may be flowed and transferred from substantially the same starting point. In this way, the sample loading distance of the sample solution can be extended to such an extent that it is beneficial to decelerate and buffer the flow of the sample solution over a relatively long distance, ensuring the consistency of sample loading.

Further preferably, the sample adding hole 110 is arranged obliquely in its axial direction with respect to the cover plate 100. According to the force on the sample solution flowing out of the sample adding tube 20 and the direction in which the liquid needs to be guided, the sample adding hole 110 is arranged obliquely a bit to render a better sample adding effect than that of a sample adding hole perpendicular to cover plate 100 when inserting the sample adding tube 20 into the sample adding hole 110 to squeeze out the sample solution, and this is more conducive to uniform and rapid distribution of the sample solution. More preferably, the sample adding hole 110, in a direction from its inlet end to outlet end, is inclined and approaches toward the place where the immunochromatographic assay components 200 are arranged. An included angle between the axial direction of the sample adding hole 110 and the cover plate 100 may be, but not limited to, 40° to 70°, such as 40°, 45°, 50°, 55°, 60°, 65°, or 70°. It can be understood that in other specific examples, the sample adding hole 110 may also be arranged perpendicularly in its axial direction with respect to the cover plate 100.

More preferably, the sample adding hole 110 has an inner diameter gradually decreased from an inlet end to an outlet end, that is, the entire sample adding hole 110 is in the shape of an inverted inverted cone (with small size at the bottom), which is adapted to the shape of the sample adding tube 20, so that the sample adding tube 20 can be fixed more stably, preventing the sample adding tube 20 from swinging forward, backward, left and right during the sample adding process, and ensuring the consistency of the sample adding position, which is beneficial to ensure the consistency of the subsequent flow of the sample solution to a sample loading zone of each of the immunochromatographic assay components 200.

In the specific example shown in FIG. 1, the cover plate 100 is provided with testing windows 120 corresponding to testing zones of the immunochromatographic assay components 200. The testing windows 120 can be configured not only to observe the testing result, but also to be ventilated, so that the sample solution can flow smoothly in the testing cavity 102.

In the specific example shown in FIGS. 1 to 3, the immunochromatographic assay component 200 is a universal long strip-shaped immunochromatographic test paper comprising a substrate 210, and a sample pad 220, a conjugate pad 230, a testing membrane 240, and an absorbent pad 250 that are arranged on the substrate 210 and connected in turn from one end to the other end of the substrate 210. The substrate 210 may be a PVC substrate. The sample pad 220 has a sample loading zone. The conjugate pad 230 contains antibodies labeled with a fluorescent group or a color developing agent, and the like. The testing membrane 240 may be a nitrocellulose membrane with a test line 242 thereon. The testing membrane 240 may be provided with a control line (not shown in the figure) thereon. The testing window 120 at least overlaps the test line 242.

In this embodiment, the sample loading portion 310 of the sample loading baseplate 300 has a multi-step structure with a height increasing stepwise. A datum surface 311 at the bottom of the multi-step structure is configured to receive the sample solution. A highest step 340 has a plurality of mounting positions configured to mount the immunochromatographic assay components 200 and other assay components (marked in the figure). The adjacent mounting positions can be arranged at intervals of, for example but not limited to, 1 mm to 4 mm. After the cover plate 100 is covered, the sample solution can flow upward from the datum surface 311, and after being intercepted and buffered by the multi-step structure, arrive at each of the mounting positions at substantially the same time.

Arriving at substantially the same time means that the time difference between the first- and the last-arrival time at the corresponding mounting position does not exceed 1.0 s, 0.6 s, 0.5 s, 0.4 s, 0.3 s, or 0.2 s. Preferably, the time difference between the first- and the last-arrival time at the corresponding mounting position does not exceed 0.3 s.

In the specific example shown in the figure, the datum surface 311 and top surfaces of the steps of the multi-step structure are all planar structures, and the datum surface 311 is arranged in parallel with the top surfaces of the steps. During the testing, the datum surface 311 and the top surface of each of the steps are arranged horizontally, which can ensure the steadiness of sample loading.

Preferably, the datum surface 311 has an isosceles triangular shape whose bottom side is connected to a side surface 321 of a lowest step 320. The datum surface 311 in the isosceles triangular shape is conducive to the uniform spread of the liquid to the bottom of the triangle. The sample solution flowing on the datum surface 311 would form an arc shape. The liquid in middle part would first contact the bottom side of the triangle, that is, middle of the bottom side of the isosceles triangle would first contact the liquid, and the both ends would later. When the flowing sample solution in middle part encounters the side surface 321 of the lowest step 320, it is slowed down and flows to the both ends, since the side surface 321 has a certain height; while the liquid on both sides of the datum surface 311 has not encountered the both ends of the side surface 321, and still maintains the original relatively fast flow rate. Thus, when the sample solution flowing along the side surface 321 to the both ends converges with the sample solution originally on both sides of the datum surface 311, the flow rate of the sample solution originally on both sides of the datum surface 311 is neutralized, that is, the flow rate of the sample solution flowing in the middle part and the flow rate of the sample solutions on both sides are balanced, and the difference is reduced.

The sample adding hole 110 corresponds to an end of the datum surface 311 far from the lowest step 320. For the datum surface 311 which is the isosceles triangle, the sample adding hole 110 corresponds to a position located between the center of gravity and the vertex angle of the isosceles triangle.

In the specific example shown in the figure, the top surface 322 of the lowest step 320 has a length gradually increasing as it approaches the second step 330 connected thereto, so that the flow rate is further reduced due to the gradually increasing width when the sample solution flows along the top surface 322, thus the flow rate difference between positions is further reduced.

Preferably, the both ends of the top surface 322 of the lowest step 320 are arc-shaped, and the arcs at the both ends are symmetrically arranged to form a steady transition buffer in order to prevent the overall flow rate control balance from being affected by partial position asymmetry.

Lengths of the top surfaces of the steps in the middle can be kept consistent with the length all over the top surface 342 of the highest step 340. Because the flow rate of the sample solution is buffered and decelerated and balanced by the datum surface 311 and the lowest step 320 which is the first step, the flow rate of the sample solution that arrives at the top surfaces of the steps in the middle and the top surface 342 of the highest step 340 is relatively low. In order to ensure the sample loading speed, the lengths of the top surfaces of the steps in the middle are kept consistent with the length all over the top surface 342 of the highest step 340, so that the sample solution can flow upwards steadily.

Further, the side surface 341 of the highest step 340 is a symmetrical cambered surface. The cambered side surface 341 gradually protrudes from both ends to the middle toward the position where the datum surface 311 is located, that is, the width of the top surface of the second-highest step gradually increases from the middle to the both ends. Due to the interception and buffering effect of the previous steps of the step structure, the sample solution arriving at the top surface of the second-highest step can substantially maintain a constant flow rate to flow forward. When the sample solution encounters the cambered side surface 341, it will quickly flow to both ends under the guidance by the cambered surface. The cambered side surface 341 can play a role in liquid guidance, and the sample solution flowing to the both ends will continue to converge with the sample solution originally flowing at both ends, thereby further balancing the flow rate and flow volume of the sample solution flowing in the middle and at both ends.

Preferably, for example, in the example shown in FIGS. 1 to 3, the sample loading portion 310 has a three-step structure, in which an initial buffer zone is formed between the datum surface 311 and the cover plate 100, a secondary transition buffer zone is formed between the lowest first step 320, middle second step 330 and the cover plate 100, and a wetting zone is formed between the highest third step 340 and the cover plate 100 and is configured to load the sample on the sample loading zone of the mounted testing sensor.

In the example shown in FIGS. 1 to 3, each of mounting positions is a long strip-shaped groove-shaped structure extending along the top surface 342 of the highest step 340. The immunochromatographic assay component 200 is an immunochromatographic test paper, which is embedded and mounted in the groove-shaped structure. Ends of the plurality of mounting positions are arranged flush, so that the sample solution can be controlled on the top surface 342 of the highest step 340 in order to reach each sample loading zone substantially at the same time. Preferably, the plurality of mounting positions are arranged in parallel, and the immunochromatographic test paper is mounted such that the sample loading end of the test paper protrudes from the top surface 342 of the highest step 340.

The cover plate 100 and the sample loading baseplate 300 can be fixed together by, but not limited to, a double-sided adhesive tape, a buckle structure or the like.

In a specific example, the cover plate 100 and the sample loading portion 310 are spaced such that when the sample solution arrives at the wetting zone (corresponding to the space between the top surface 342 of the highest step 340 and the cover plate 100 in FIGS. 1 to 3), it will flow along the surface of the sample loading portion 310 toward the position where the sample loading zone of the immunochromatographic assay component 200 is located under the propulsion of capillary action.

Preferably, the wetting zone has a height (that is, the distance between the cover plate 100 and the top surface 342 of the highest step 340) not greater than 2 mm. Through experimental research, it is found that when the height of the wetting zone is greater than 2 mm, laminar flow is not easy to be formed in the wetting zone, bubbles are easy to be formed in the wetting zone, and thus it is difficult to produce capillary action. Further preferably, the height of the wetting zone is between 0.1 mm and 1 mm. When the height of the wetting zone is less than 0.1 mm, the height is difficult to be controlled, the machining and the process are greatly difficult, and the sample loading rate is affected. More preferably, the height of the wetting zone is between 0.25 mm and 0.7 mm Within this range, the liquid laminar flow effect is better, and bubbles are not easy to generate.

By this structural design, the sample solution can flow in the corresponding zone under capillary action, in particular, the sample solution between the top surface 342 of the highest step 340 and the cover plate 100 can quickly cover the top surface 342. This not only allows all the sample solution to be loaded to the assay component under capillary action, but also renders a significantly increased sample loading speed, which reduces the problem of the sample solution flow rate reduction caused by the interception and buffering effect of the multi-step structure, which affects the efficiency of sample loading, thereby improving the efficiency of sample loading and thus the efficiency of testing.

In the specific examples shown in FIGS. 1 to 3, due to the interception and buffering effect of the multi-step structure, the sample solution can substantially arrive at the long strip-shaped immunochromatographic test papers at the same time. The sample pad 220, after being in contact with the sample solution, can quickly absorb the sample solution. The absorbed liquid completes the sample processing process in this zone, and then passes through a conjugate pad 230 where antigens immunologically bind antibodies, with fluorescent groups conjugated. When the liquid flows through the testing membrane 240, the immunocomplex specifically bind to the antigen and antibody bound on the nitrocellulose membrane in advance. The excess unreacted material is absorbed by the absorbent pad 250. The fluorescent groups gathered on the test line 242 of the testing membrane 240 can show the test result. In a multi-item test, the basic structure of each of the immunochromatographic assay components 200 is the same except for the different antigen and antibody thereon. Since the antigen and antibody do not affect the water absorption effect, it is ensured that contacting each of the immunochromatographic assay components 200 with the sample at the same time in order to cause adsorption can be equivalent to uniformly distributing the sample to each immunochromatographic assay component 200. The experimental test results show that the immunochromatographic assay device 10 has an error of parallelism less than 5%, and thus can meet the needs of in vitro immunochromatographic diagnostic testing.

The immunochromatographic assay device can directly use the original immunochromatographic assay components 200 without changing the original single immunochromatographic assay component 200, and can perform multi-item tests at the same time by a single sample loading. The immunochromatographic assay device has simple structure and low cost, and is easily processed and manufactured, and realizes convenient sample loading, short time-consuming, strong stability, and high accuracy of uniformly distributing sample amounts.

Figure 4:
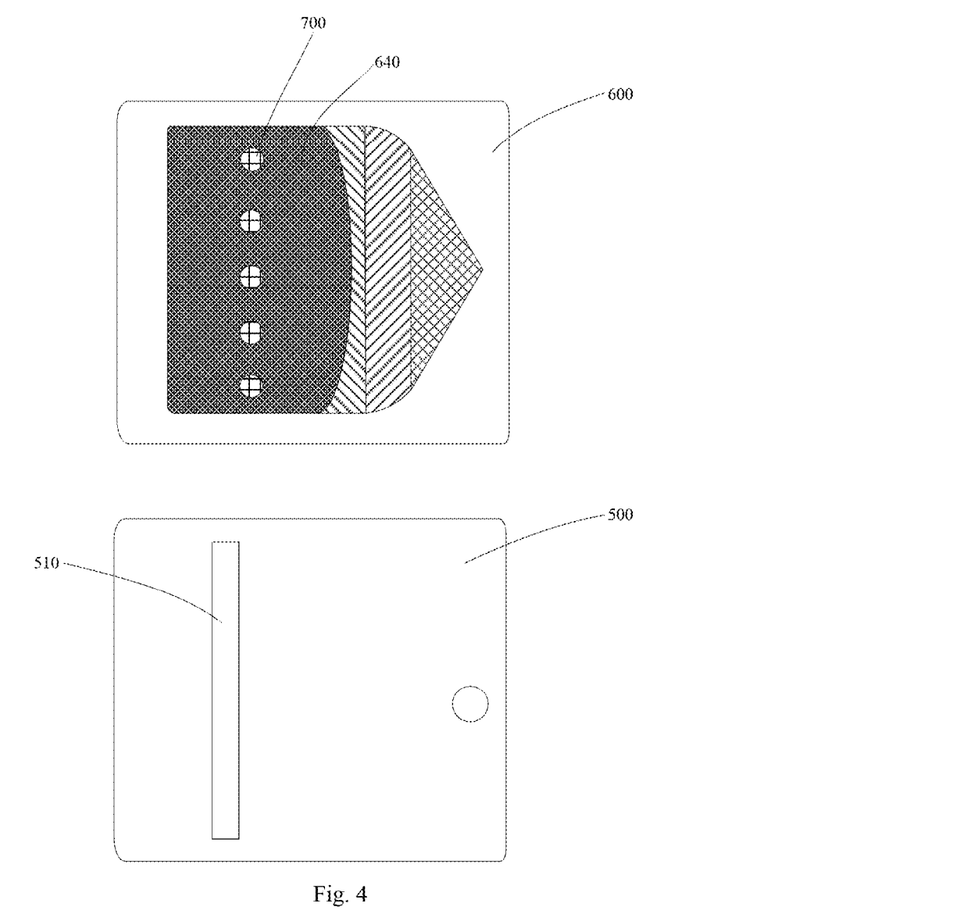
FIG. 4 is a partial exploded view of an immunochromatographic assay device according to another embodiment of the present disclosure.
Figure 5:
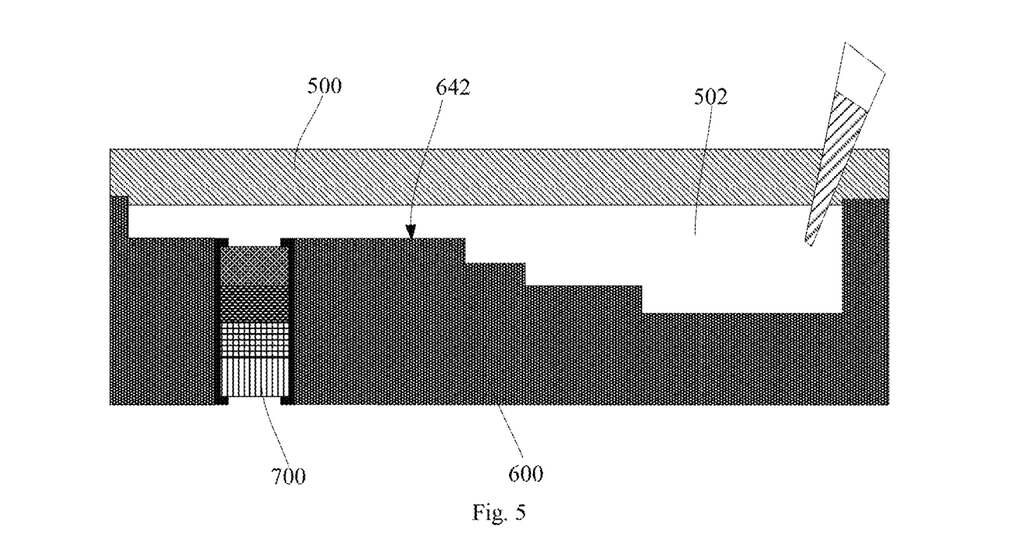
FIG. 5 is an after-assembly cross-sectional view of the immunochromatographic assay device shown in FIG. 4.
Figure 6:
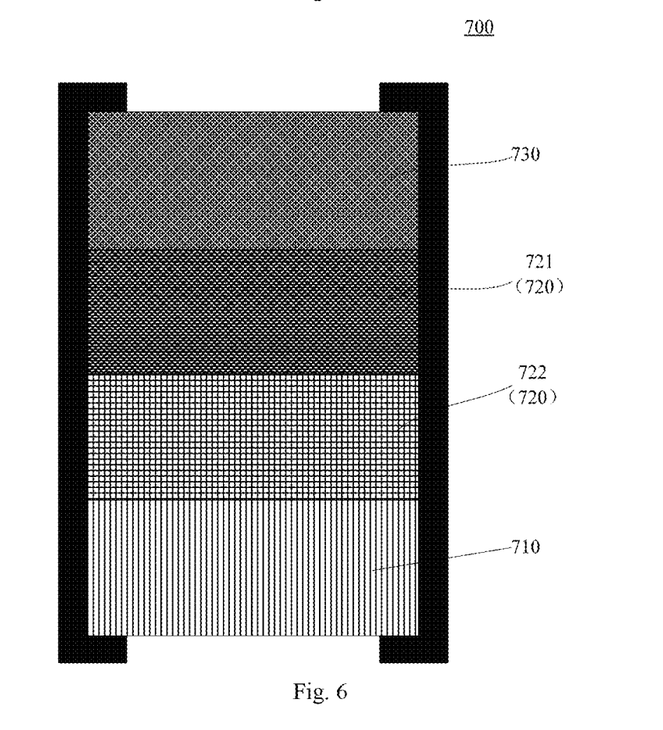
FIG. 6 is a structural schematic diagram of an immunochromatographic assay component in the immunochromatographic assay device shown in FIG. 5.

In other embodiments, as shown in FIGS. 4 to 6, each of the mounting positions may also be a cylindrical hole structure with an axial direction perpendicular to the top surface 642 of the highest step 640 and with openings at both ends, configured to embed and mount an immunochromatographic assay component 700, such as a dry chemical test paper, which has a laminated structure. The opening at the upper end is configured to form a sample loading zone to allow the sample solution to flow into, and the opening at the lower end constitutes a testing window.

The immunochromatographic assay component 700 having the laminated structure comprises a supporting layer 710, a reaction layer 720, and a diffusion layer 730 stacked in sequence. The diffusion layer 730 has a sample loading zone. The reaction layer 720 contains a reaction reagent capable of reacting with target substance and a color developing agent.

Specifically, the reaction layer 720 comprises a reagent layer 721 and a color developing layer 722 that are stacked. The color developing layer 722 is closer to the supporting layer 710. The reagent layer 721 contains a reaction reagent capable of reacting with the target substance, and the color-developing layer 722 contains a color developing agent; or vice versa.

Preferably, the cover plate 500 is provided with a vent hole 510 in an zone corresponding to the immunochromatographic assay component 700, which communicates with a testing cavity 502 in order to facilitate ventilation and ensure a balanced air pressure in the testing cavity 502 so that the sample solution flows smoothly.

The sample loading baseplate of the present disclosure is not limited to be configured to load sample on the immunochromatographic assay component, for example, on the above-mentioned long strip-shaped immunochromatographic test paper or the dry chemical immunochromatographic test paper having the laminated structure, and can also be configured to load sample on other assay components, such as electrochemical assay components and the like. By using the cover plate mating with the sample loading baseplate, uniform and consistent sample loading can be realized for different assay components.

In the design of the above immunochromatographic assay device, the sample loading zone is provided with the sample loading portion with a multi-step structure. The sample loading portion has the multiple steps with different heights.

The datum surface is configured to receive the sample solution. The cover plate is closed. After the sample solution falls on the datum surface, it will flow upwards. Due to the interception and buffering effect of the multi-step structure, the sample solution that finally flows to the top surface of the highest step can arrive at the sample loading zone of each of the immunochromatographic assay components substantially at the same time, so that multiple immunochromatographic assay components can substantially receive the sample solution at the same time. There is no problem regarding the unity on time and sample parallel lines, rendering a high test accuracy. Also, sample loading is required only once, resulting in a high testing efficiency and a relatively small risk of error. During a test performed by the immunochromatographic assay device, each of the immunochromatographic assay components performs the test independently and the sample is loaded at the same time. There is no mutual interference between the assay components, which is further conducive to increase the accuracy of the test result.

Further, the immunochromatographic assay device of the present disclosure is provided with the wetting zone with a certain length on the upstream of the sample loading zone of the immunochromatographic assay component. When the sample solution flows to the wetting zone, capillary action will be produced to push the sample solution to flow in the wetting zone. This can not only increase the flow rate of the sample solution in this zone, but also realize the substantially simultaneous sample loading on the assay components in different mounting positions, which is beneficial to improve the consistency and uniformity of sample loading.

For the conventional multi-card immunochromatographic assay devices, it is difficult for the immunochromatographic assay components in different mounting positions to be loaded at the same time due to the inconsistency of sample loading. Also, nonuniform loading amount leads to only 3-in-one or 4-in-one test can be performed, and 5-in-one or more-in-one test can not be perfomed. Using the sample loading baseplate with the above-mentioned structure and/or controlling the distance between the sample loading baseplate and the cover plate to produce capillary action in the wetting zone, 5-in-one or 6-in-one test can be realized in the immunochromatographic assay device of the present disclosure with good consistency of sample loading and effectively improved accuracy and reliability of testing results.

Referring to FIGS. 7a and 7b, FIGS. 8a and 8b, and FIGS. 9a and 9b, the sample loading effect of sample loading baseplates with different structures is compared and analyzed.

Figure 9A:
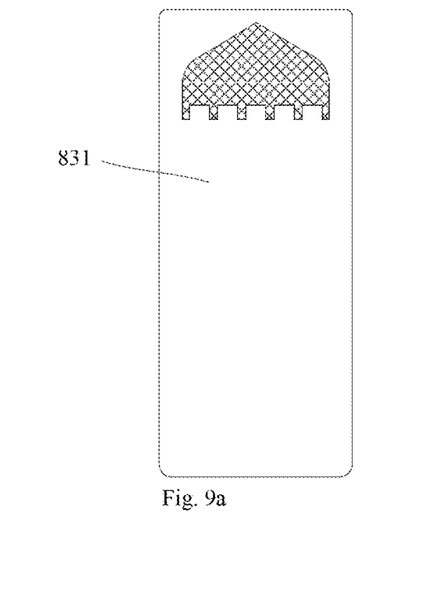
Figure 9B:
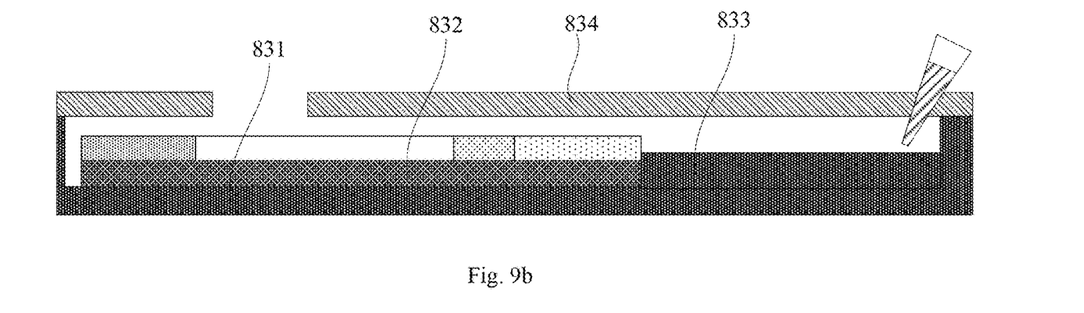

1. Comparison and Analysis for Height of Wetted Zone in Contact with Sample Loading Zone of Assay Components A sample loading baseplate 831 with no stepped structure as shown in FIGS. 9a and 9b is taken as an example. A sample loading portion 833 between a position below a sample adding hole and a sample loading zone of an immunochromatographic assay component 832 has a flat structure. A wetting zone is formed between the sample loading portion 833 and a cover plate 834.

The wetting zone is controlled to be in a height of 0.1 mm, 0.25 mm, 0.5 mm, 0.7 mm, 1 mm, 1.5 mm, 3 mm, 3.5 mm, 4 mm and 4.5 mm respectively, and the 5-in-one immunochromatographic test paper is observed for its loading condition.

The results show that compared to the wetting zone with the heights of 3 mm, 3.5 mm, 4 mm and 4.5 mm, the consistency of sample loading is significantly improved when the wetting zone has a height of 0.1 mm, 0.25 mm, 0.5 mm, 0.7 mm, 1 mm, 1.5 mm, and is especially better when the height is 0.25 mm, 0.5 mm or 0.7 mm.

The slow motion of videos show that in the cases where the height is 0.1 mm, 0.25 mm, 0.5 mm, 0.7 mm, 1 mm, 1.5 mm, the sample solution can flow quickly in the wetting zone. Through analysis, it can be determined that capillary action is formed in this zone, which is conducive to the rapid flow of the sample solution and thus the rapid sample loading, and the time difference of sample loading of assay components from different mounting positions is reduced to a certain extent. However, in the cases where the height of the wetting zone is 3 mm, 3.5 mm, 4 mm, or 4.5 mm, bubbles are formed in the wetting zone, which affects the capillary action, thus further affects the consistency of sample loading.

In the same way, the sample loading baseplates shown in FIG. 1 or FIG. 4, FIGS. 7a and 7b, FIGS. 8a and 8b have also been tested with different heights of wetting zones. The results are substantially the same as those of the structure shown in FIGS. 9a and 9b.

Therefore, by forming a wetting zone on the upstream of the sample loading zone of the assay component and controlling the height of the wetting zone, the sample solution can produce capillary action when entering the wetting zone to increase the flow rate of the sample solution, and thus the time difference of sample loading at different positions is reduced to a certain extent, which improves the consistency of sample loading.

2. Experiment and Analysis of Influence of Sample Loading Portions with Different Structures on Consistency of Sample Loading The structure of the buffer zone and wetting zone, the arc of the buffer zone and the number of buffer steps all have an influence on the effect of the uniform distribution the liquid. The sample loading baseplates 300 and 600 shown in FIGS. 1 and 4 are a preferred embodiment in the present disclosure. This design has the smallest deviation CV value in the uniform distribution of the liquid, less than 3%, and has good stability. After testing, a probability that one or two of the five immunochromatographic assay components is/are not loaded with sample is less than 1%.

Figure 7A:
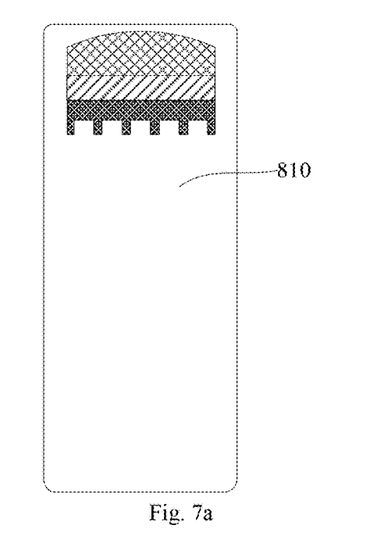
FIGS. 7a and 7b, 8a and 8b, and FIGS. 9a and 9b are respectively a top view and a corresponding cross-sectional view of buffer structures having other stepped structures.
Figure 7B:
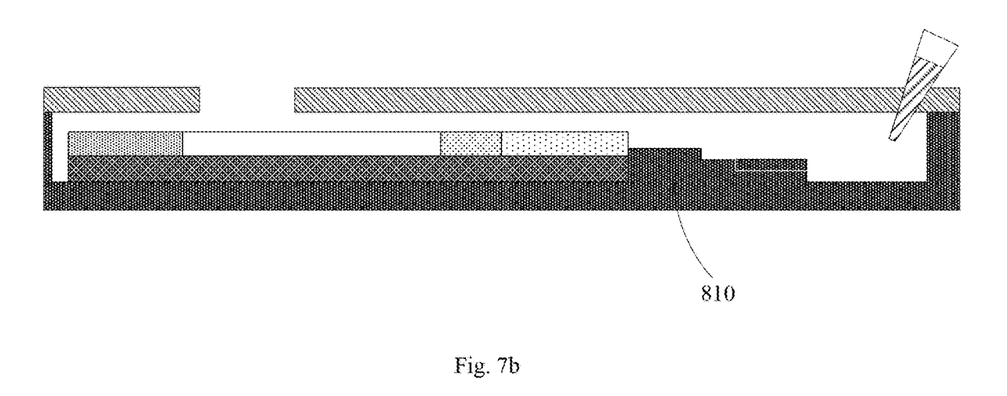

Additionally, in the sample loading baseplate 831 shown in FIGS. 9a and 9b, due to lack of a buffer zone, one in the middle of the five immunochromatographic assay components would contact the liquid first, leading to a relatively large CV deviation in the uniform distribution. For a sample loading baseplate 810 shown in FIGS. 7a and 7b, which has an arc-shaped datum surface, compared with the isosceles triangle shown in FIGS. 1, 4 and 9a, the experimental result shows that the two immunochromatographic assay components located on outermost sides may be relatively easy to fail to be loaded with sample. Triangle is beneficial to guide the liquid to flow to the both ends, avoiding the phenomenon of the liquid not loading at both ends. Therefore, the sample loading baseplate 810 shown in FIGS. 7a and 7b is feasible, but has a sample loading effect slightly worse than that of the sample loading baseplates 300 and 600 shown in FIGS. 1 and 4, but significantly better than that of the sample loading baseplate 831 shown in FIGS. 9a and 9b.

Figure 8A:
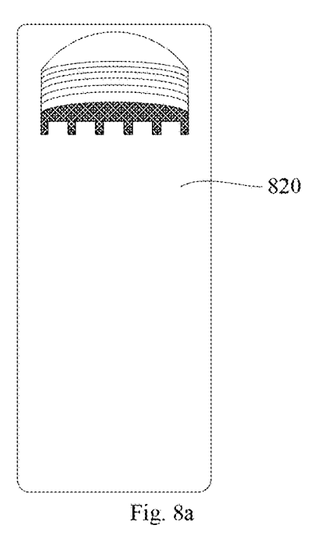
Figure 8B:
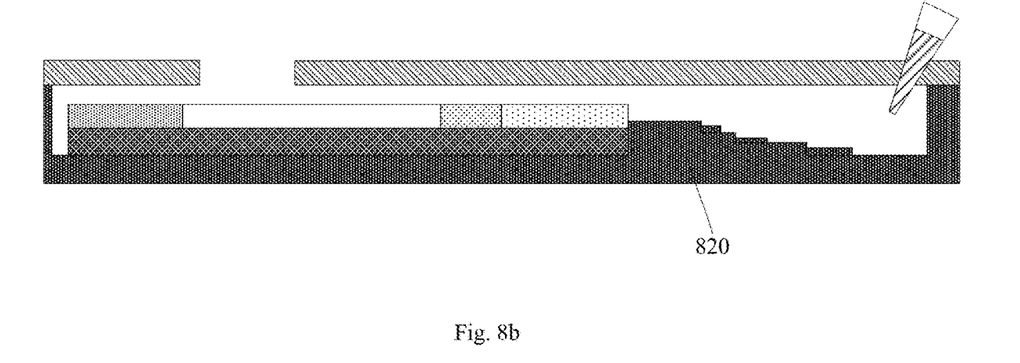

In a sample loading baseplate 820 shown in FIGS. 8a and 8b, there are five buffer zones. Due to the dense buffer zone, the resistance to the upward flow of the liquid is relatively large, so liquid may be failed to enter the wetting zone (that is, the top surface of the highest step), relatively increasing the probability of failing to load. Furthermore, due to the larger depth of the buffer zone, the flow may be cut off or the liquid on the datum surface and in the first buffer zone above the lowest step may not be completely absorbed when the immunochromatographic assay component absorbs liquid. Part of the residue will directly affect the accuracy of sample loading. Therefore, the sample loading baseplate 820 shown in FIGS. 8*a* and 8*b* is feasible, but has a sample loading effect slightly worse than that of the sample loading baseplates 300 and 600 shown in FIGS. 1 and 4, but significantly better than that of the sample loading baseplate 831 shown in FIGS. 9*a* and 9*b*.

Therefore, generally speaking, regarding the structural design of the sample loading portion, a suitable buffer zone has a direct effect on the even distribution of liquid. Many simulations and experiments show that the embodiments shown in FIGS. 1 and 4 is more preferable, with very small error in the uniform distribution, and extremely low probability of loading failure. In some cases, the embodiments as shown in FIG. 7*a* and FIG. 8*a* are also feasible.

In summary, the sample loading consistency of the testing structure on different mounting positions can be improved by controlling the height of the wetting zone to produce capillary action in the wetting zone, or by suitably designing the structure of the buffer zone to improve the even distribution of liquid. Preferably, the capillary action and the suitable design of the structure of the buffer zone can be combined to further improve the sample loading effect.

It can be understood that for the assay device in which capillary action can be formed in the wetting zone, the sample loading portion of the sample loading baseplate may not be limited to have the stepped structures shown in FIG. 1, 4, 7*a* or 8*a*, but may also has the flat structure as shown in the FIGS. 9*a* and 9*b*, which can also improve the sample loading consistency of different assay components to a certain extent compared with the conventional assay devices and have the simple structure and reduced interference between different assay components, which is beneficial to improve the accuracy of the test result. For the assay device that uses capillary action to improve the consistency of sample loading, the height of the wetting zone is preferably no more than 2 mm, such as between 0.1 mm and 1 mm, and more preferably between 0.25 mm and 0.7 mm.

The technical features in the above-mentioned embodiments can be combined arbitrarily. In order to make the description concise, all possible combinations of the various technical features may not be described in the above-mentioned embodiments. However, they should be regarded as within the scope of this specification as long as there is no contradiction in the combination of these technical features.

The above-mentioned examples only represent several embodiments of the present disclosure with more specific and detailed descriptions, but should not be deemed limiting the scope of the present disclosure. It should be pointed out that several modifications and improvements can be made without departing from the concept of the present disclosure for those of ordinary skill in the art, and are all within the protection scope of the present disclosure. Therefore, the protection scope of the present disclosure should be subject to the appended claims.

What is claimed is:

1. A sample loading baseplate comprising a sample loading portion; wherein the sample loading portion is a multi-step structure with a height increasing stepwise, wherein a datum surface located in the bottom of the multi-step structure is configured to receive the sample solution and a highest step of the multi-step structure has a plurality of mounting positions configured to mount assay components, the adjacent mounting positions being arranged at intervals, wherein the datum surface is an isosceles triangular shape whose bottom side is connected to a side surface of a lowest step, wherein a top surface of the lowest step has a length gradually increasing as it approaches a higher step connected thereto, and wherein both ends of the top surface of the lowest step are arc-shaped, and the arcs at the both ends are symmetrically arranged.

2. The sample loading baseplate according to claim 1, wherein when the sample loading portion is provided with a flat cover plate that is capable of covering the sample loading portion, and a sample solution is loaded to a position of the datum surface near its front end, the sample solution is capable of arriving at each of the mounting positions at substantially the same time after being intercepted and buffered by the multi-step structure.

3. The sample loading baseplate according to claim 1, wherein the test component is an immunochromatographic test paper with a sample loading zone located on the mounting position.

4. The sample loading baseplate according to claim 1, wherein the plurality of mounting positions satisfy at least one of the following requirements:
   ends of the plurality of mounting positions are arranged flush to each other;
   the plurality of mounting positions are arranged in parallel; and
   the adjacent mounting positions are arranged at intervals of 1 mm to 4 mm.

5. The sample loading baseplate according to claim 1, wherein the datum surface and top surfaces of steps of the multi-step structure are all planar structures, and the datum surface is arranged in parallel with the top surfaces of the steps.

6. The sample loading baseplate according to claim 1, wherein lengths of top surfaces of steps in the middle are kept consistent with the length all over the top surface of the highest step.

7. The sample loading baseplate according to claim 1, wherein a side surface of the highest step is a symmetrical cambered surface, and the cambered side surface gradually protrudes from both ends to the middle toward the position where the datum surface is located.

8. An immunochromatographic assay device comprising a cover plate, immunochromatographic assay components, and the sample loading baseplate according to claim 1; wherein the cover plate mates with the sample loading baseplate to define a testing cavity; a sample loading portion is located in the testing cavity; the cover plate is provided with a sample adding hole corresponding to a datum surface of the sample loading portion; and the immunochromatographic assay components are a plurality of immunochromatographic assay components, and sample loading zones of the plurality of immunochromatographic assay components are mounted on the plurality of mounting positions.

9. The immunochromatographic assay device of claim 8, wherein the sample adding hole is closed to an end of the datum surface far from a lowest step.

10. The immunochromatographic assay device of claim 8, wherein the sample adding hole is arranged obliquely in its axial direction with respect to the cover plate.

11. The immunochromatographic assay device of claim 8, wherein the sample adding hole has an inner diameter gradually decreased from an inlet end to an outlet end.

12. The immunochromatographic assay device of claim 8, wherein the cover plate and the sample loading portion are spaced such that when the sample solution arrives at a space between a top surface of the highest step and the cover plate, the sample solution is capable of flowing along a surface of the sample loading portion toward a position where the sample loading zone of the immunochromatographic assay component is located under the propulsion of capillary action.

13. The immunochromatographic assay device of claim 12, wherein a distance between the top surface of the highest step of the sample loading portion and the cover plate is not greater than 2 mm.

14. The immunochromatographic assay device according to claim 8, wherein each of the mounting positions is a long strip-shaped groove-shaped structure extending along a top surface of the highest step, configured to embed and mount a long strip-shaped immunochromatographic assay component.

15. The immunochromatographic assay device of claim 14, wherein the immunochromatographic assay component comprises a substrate, and a sample pad, a conjugate pad, a testing membrane, and an absorbent pad that are arranged on the substrate and connected in turn from one end to the other end of the substrate, wherein the sample pad has a sample loading zone, and the testing membrane has a test line.

16. The immunochromatographic assay device according to claim 8, wherein each of the mounting positions is a cylindrical hole structure with an axial direction perpendicular to a top surface of the highest step and with openings at both ends, configured to embed and mount an immunochromatographic assay component having a laminated structure; wherein the opening at the upper end is configured to allow the sample solution to flow into the sample loading zone, and the opening at the lower end constitutes a testing window.

17. The immunochromatographic assay device of claim 16, wherein the immunochromatographic assay component comprises a supporting layer, a reaction layer, and a diffusion layer stacked in sequence, the diffusion layer having the sample loading zone and the reaction layer containing a reaction reagent capable of reacting with a target substance and a color developing agent.

* * * * *